United States Patent [19]

Kuderna, Jr.

[11] 3,954,963

[45] May 4, 1976

[54] AIR REODORANT COMPOSITIONS

[75] Inventor: Jerome G. Kuderna, Jr., Modesto, Calif.

[73] Assignee: Shell Oil Company, Houston, Tex.

[22] Filed: Mar. 4, 1974

[21] Appl. No.: 448,126

[52] U.S. Cl. ................................ 424/76; 239/60; 252/522

[51] Int. Cl.² .................. A61L 9/00; A61L 9/04; A61L 13/00

[58] Field of Search ...................... 424/76; 252/522

[56] References Cited

UNITED STATES PATENTS

| | | | |
|---|---|---|---|
| 2,691,615 | 10/1954 | Turner et al. | 424/76 |
| 2,865,806 | 12/1958 | Bulloff | 424/76 |
| 2,927,055 | 3/1960 | Lanzet | 424/76 |
| 3,655,129 | 4/1972 | Seiner | 424/76 X |
| 3,688,985 | 9/1972 | Engel | 239/54 |
| 3,821,413 | 6/1974 | Hellyer, Jr. | 424/76 X |

FOREIGN PATENTS OR APPLICATIONS 1,241,914   8/1971   United Kingdom

OTHER PUBLICATIONS

The Merck Index. 8th Ed. (1968) pp. 214, 215, 654.

*Primary Examiner*—Jerome D. Goldberg
*Assistant Examiner*—Allen J. Robinson

[57] ABSTRACT

Long lived, slow release air reodorant compositions comprise polyvinyl acetal resins gelled with an oxygenated terpene. The gels may additionally contain one or more fragrances or perfumes, diluents or adjuvants, a minor amount of water, as well as dyes, surfactants, deodorants and other conventional additives.

11 Claims, No Drawings

AIR REODORANT COMPOSITIONS

RELATED APPLICATIONS

This application is related to copending Serial No. 448,127 filed of even date herewith which claims similar organically gelled air reodorants differing primarily in the gelling agent used.

BACKGROUND OF THE INVENTION

Air reodorizing or deodorizing compositions in gel form are well-known in the art. Primarily they comprise an aqueous medium containing a volatile fragrance and a small amount of a gelling agent which renders the compositions in a gel-like or semi-solid form. These compositions are popular in that they are easy to handle, and on exposure to air, the aqueous medium gradually evaporates from the gel releasing the fragrance into the surrounding atmosphere. Aqueous gels of this type are claimed in U.S. Pat. Nos. 2,691,615 and 2,927,055 and in British patent 1,241,914.

One difficulty with most aqueous gels is that they are relatively short-lived. This is because of the rapid rate of release of water and fragrance from gels of this type, and because only a small part of the gel, e.g., from 1 to 10% of the aqueous phase, is available as a fragrance for acting as a reodorant. Also because of the rapid rate of release of water, aqueous gels are necessarily large in size, thus limiting holder design and increasing shipping costs. Moreover, when subjected to low temperatures the aqueous gels might freeze which will result in excessive bleeding or gel decomposition upon thawing.

As used in this application, the term "reodorant" means an air freshener whereby the odors in the surrounding atmosphere are masked or overcome by the fragrance emitted from the air freshener. As so defined this term is intended to include true deodorants which react with or destroy the odor which is to be overcome.

Various types of non-aqueous air fresheners have also been proposed. For example, U.S. Pat. No. 2,865,806 discloses in air odor control agent prepared by blending a menthadiene compound, and preferably an added antioxidant, with a selected solidifying agent at an elevated temperature and then cooling the blend. The solidifying agents are certain polyethylenes and ethyl celluloses. The menthadiene compounds are monocyclic terpenes containing nonconjugated double bonds, not more than one of which occurs outside the six carbon ring, i.e., d- or l-limonene or racemic mixtures (dipentene) may be used. An important feature of the disclosed non-aqueous air fresheners is said to be that bleeding or exudation of the dipentene to the surface of the molded product occurs which facilitates its removal from the mold.

While bleeding or exudation may be beneficial in aiding the release of the molded product, these properties are generally not desirable to the consumer since syneresis or bleeding during use can cause liquid droplets to come in contact with fabrics, furniture and other finishes within the home which may cause staining or other damage. Hence, from a consumer point of view, it is desirous to have a solid air reodorant which is storage stable, dry to the touch and yet which permits adequate release of a fragrance into the surrounding atmosphere over a sustained period of time.

An attempt to achieve these results is outlined in U.S. Pat. 3,688,985 wherein a pre-formed plastic object is soaked in a stable aqueous emulsion containing an essential oil and a surfactant to impregnate the resin with the essential oil thereafter drying the resin to yield a dry impregnated resin which gradually releases the essential oil into the surrounding atmosphere.

Also mentioned in U.S. Pat. No. 3,688,985 is British Pat. No. 599,237 wherein an essential oil is combined with a plasticized synthetic resin by dispersing the resin in a plasticizer, including the essential oil, which is gelled by heat to form the desired article. However, as reported, the essential oils when heated to the gelling temperatures break down, thereby causing a change in the chemical properties of the essential oil so that they can no longer be useful for the intended purpose.

Thus it can be seen that although considerable effort has been devoted to the development of stable, long-lived air reodorant formulations, considerable problems remain and there is continuing need for improved products. The present invention is directed to one such class of highly advantageous air reodorant compositions.

STATEMENT OF THE INVENTION

It has now been found that storage stable, dry, long lived air reodorant formulations can be made comprising certain resin bases which have been gelled with a particular class of organic gelling agents. More specifically, it has been found that when polyvinyl acetal resins are combined with cyclic or acylic oxygenated terpenes, i.e., terpene aldehydes, ketones or alcohols, unique gels result having highly beneficial properties as air reodorants. Such gels may additionally contain one or more fragrances or perfumes, organic diluents or adjuvants, a minor amount of water, as well as dyes, surfactants, deodorants and other conventional additives. The gels generally can be prepared at room temperature but may be heated to an elevated temperature below that at which the gellant, diluent or fragrance decomposes. The resulting gels are dry and rubbery in appearance, are storage stable, and release an effective amount of fragrance over extended periods of time in addition to being very compact.

DETAILED DESCRIPTION OF THE INVENTION

Fundamental to this invention is the discovery that oxygenated terpenes, i.e., terpenes containing a carbonyl or a hydroxyl function, i.e., terpene aldehydes, ketones or alcohols, act as gelling agents for polyvinyl acetal resins having the following properties:

1. It must be compatible with the oxygenated terpene gelling agent.
2. It should have a molecular weight of from about 30,000 to about 1,000,000, and preferably from about 180,000 to about 300,000.
3. It must contain free hydroxyl groups. While it is not precisely known by what mechanism the oxygenated terpene interacts with the polyvinyl acetal resin, it is believed that the mechanism is that of hydrogen bonding between the carbonyl or hydroxyl function of the terpene and the free hydroxyl functions of the resin. Gel structures so formed have the capability of absorbing relatively large amounts of other liquids including water if adequately solubilized. Therefore although the gelling agents themselves, i.e., the oxygenated terpenes, are typically fragrances, other fragrances may also be added to the gels of the invention thereby providing the opportunity to vary the quality, quantity and intensity of the odor. In other words, practically any odor desired may be produced in the gels of this invention by appropriate selection of fragrance and diluent.

Among the polyacetal resins that can be used according to the invention are polyvinyl formal, polyvinyl acetal and polyvinyl butyral resins. In general useful polyvinyl acetal resins are those consisting essentially of repeating vinyl acetal, vinyl alcohol and vinyl acetate groups represented by the following chemical structure:

cryptone, carvotanacetone, carvenone, dihydrocarvone, piperitone, pulegone, the santolihenones, carvone, piperitenone, sylvecarvone and diosphenol. Typical of the monocyclic terpene alcohols are methol, carvomenthol, terpineols and terpinenols. Terpene aldehydes and ketones have generally been found to give more stable gels than corresponding alcohols and hence are preferred. Particularly preferred are carvone and menthone because of their commercial availability and acceptability as fragrances.

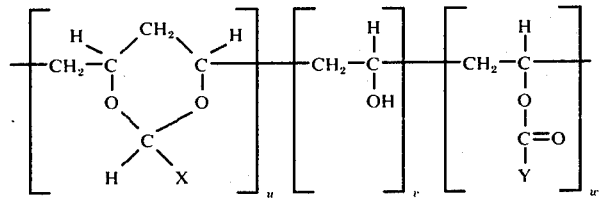

wherein X is H, alkyl, haloalkyl or hydroxyalkyl of 1–8 carbon atoms, alkenyl of 2–8 carbon atoms, halogen or hydroxyl; Y is alkyl of 1–9 carbon atoms; and u, v and w indicate the relative percent by weight of the vinyl acetal, vinyl alcohol and vinyl ester groups, respectively, in the resin.

In order to maintain hydrogen-bonding between the polyvinyl acetal resin and carbonyl-containing terpene as previously discussed, it is necessary that the resin contain a certain number of free hydroxyl groups which will vary somewhat from polymer to polymer. In general, the relative percentage of vinyl alcohol groups (v in the above formula) should be at least 10, preferably from about 15 to about 25, most preferably from about 17 to about 21. The percentage of vinyl acetal groups ($u$ in the above formula) can be from about 30 to about 90, but preferably is from about 75 to about 85, while the percentage of vinyl ester groups (w in the above formula) can vary from 0 to about 30, but preferably is from 0 to about 5. The sum of $u$, $v$ and $w$ equals 100.

Polyvinyl acetal resins having molecular weights and vinyl acetal, vinyl alcohol and vinyl ester contents within the above specified ranges can be prepared by well known methods and are commercially available. Among the polyvinyl resins which can be employed in the reodorant gel compositions of the invention, polyvinyl butyrals have been found to be particularly advantageous.

Oxygenated terpene gellants which are employed in accordance with the invention include acyclic or monocyclic terpenes containing either a carbonyl function, i.e., terpene aldehydes and ketones, or a hydroxyl function, i.e., terpene alcohols. Such terpenes (also referred to as terpenoids) and their source or method of manufacture are described in Kirk-Othmer, Encyclopedia of Chemical Technology, 2nd ed., Vol. 19, pp 803–833. In general, the terpene aldehydes, ketones and alcohols employed in the present invention will have ten carbon atoms and include, for example, citronellal and citral, both of which are acyclic terpene aldehydes; 2,6-dimethyl-7-octene-4-one, tagetone and artemesia ketone which are acyclic terpene ketones; and citronellol and geraniol which are acyclic terpene alcohols. Representative of the monocyclic terpene aldehydes are phellandral and perillaldehyde. Typical of the monocyclic terpene ketones are menthone, carvomenthone, The acyclic or monocyclic oxygenated terpenes may be brought into contact with the polyvinylacetal resins as a separate ingredient, or they can be present as a component of the perfume or fragrance which is added to the polyvinylacetal resin. In other words the means by which the terpene gellant and polyvinyl acetal are brought into contact is immaterial as long as the requisite amount of each are present. Hence, as will be apparent to those skilled in the art, perfumes which contain oxygenated terpenes as part of their formulation can be suitably employed to form gel compositions in accordance with the present invention, without the need for separate oxygenated terpene addition.

Various diluents may be added to the compositions of this invention and act in many ways to enhance its acceptability. For example, diluents are usually cheaper than the gelling agent and/or fragrances used and at the same time serve to extend the useful life of the gel compositions. In general, any organic diluent having a boiling point of between about 175° and 250°C and which is mutually compatible with the gellant and fragrance can be used in the present invention. As previously mentioned, these diluents should have a pleasant aroma and blend well with the fragrance and gelling agent. Typical of the diluents that may be added in the invention are the menthadienes such as d- and 1-limonene. Other diluents include beta pinene, amyl acetate, isopropyl acetate, alpha terpineol, 2-ethylhexyl alcohol and octyl acetate. Some diluents, for example d-limonene, have a citrus odor. Other diluents used in combination with limonene, for example, 2-ethylhexyl alcohol, tend to mask the citrus odor of limonene and therefore make the added fragrance more distinct. In addition, minor amounts of water, e.g., up to about 20% by weight of the total composition, can also be employed as a diluent if adequately solubilized, e.g., by the addition of one or more surfactants. In general, the organic diluents act the same as water in an aqueous gel formulation except that the organic diluent in itself is a fragrance as well as a carrier. Moreover, the diluent tends to come out of the organically gelled formulation at a slower rate than does water from an aqueous air reodorizer, thereby considerably extending the life of the organically gelled air reodorizer.

The fragrances or perfumes which may be added to the compositions of this invention are many and varied and it would serve little purpose to try to elucidate each and every fragrance which can be utilized herein. The only essential requirements for the fragrances herein employed are that they be mutually compatible with the gellant and resin (and diluent if employed), and that they have mutually compatible odors. In general, the fragrances will have a boiling point between about 150°–350°C, preferably 200°–300°C and will add body and contribute a sophisticated quality to the odor of the gel composition.

Suitable fragrances may be comprised of single chemical constituents or may be blends of many different chemical compounds which may be of natural or synthetic origin. These fragrances include alcohols, aldehydes, ethers, ketones, esters and frequently also hydrocarbons which are combined in fixed proportions so that the odor of the individual compounds will combine to produce a harmonious fragrance. In perfumery practice these compounds are combined by the blending of natural essential oils, gums, resins, animal derivatives, natural isolates and synthetic chemicals. In practice, most perfumes are blends of many types of chemicals and their composition is of a proprietary nature and hence normally designated by trade name rather than by chemical composition. Because of this, and since the efficacy of the present gels is not dependent on the use of a particular perfume, no attempt has been made to define the perfume with the same chemical preciseness as the gellant and resin, nor would it be possible to do so.

From the foregoing it can be seen that the only essential components of the present reodorant compositions are the oxygenated terpene gellants and the polyvinyl acetal resin, since the terpene can serve as the fragrance and/or diluent as well as the gellant. However, as previously discussed, it is generally desirable from an economic standpoint to employ an additional diluent, and from a fragrance quality standpoint to employ an additional fragrance (perfume) to supplement and reinforce the odor of the terpene gellant and/or diluent.

As also mentioned, oxygenated terpenes can be present as a component of a particular perfume or fragrance formulation, in which event suitable reodorant gels can be formed from the terpene-containing perfume and polyvinyl acetal resin alone, without the need for further terpene gellant addition.

As will also be obvious from the above description, the major proportion of the liquid in the gels of the present invention is available as a reodorant which has a distinct advantage over aqueous gels wherein only a minor portion of the liquid phase is available for air freshening purposes, the water serving only as a carrier.

In general, the reodorant gel compositions of this invention comprise from about 10 to about 40% by weight of polyvinyl acetal resin and from about 5 to about 90% by weight of the oxygenated terpene gellant. The reodorant gels may additionally contain from 0 to about 60% by weight of organic diluent, from 0 to about 90% by weight of a perfume and from 0 to about 20% water. Obviously the above proportions are heavily weighted at the upper limits of diluent, perfume and gellant in that, as previously discussed, it is possible for the carbonylcontaining terpenes to function as both perfume and diluent as well as gellant. Likewise it is also possible for the fragrance or perfume to also serve as diluent or even gellant, provided it contains the requisite amount of oxygenated terpene.

Within preferred liminits the resin will normally comprise about 15 to about 30% by weight of the composition with the gellant comprising about 10 to about 30% by weight of the composition. The organic diluent, in preferred ranges, will be present in amounts varying from about 10 to about 50% by weight, whereas the fragrance or perfume will be present in an amount of about 1 to about 60% by weight, while water will be present in an amount of from 0 to about 10% by weight.

The amount of resin in the composition is critical to its function. Too little resin will cause the composition not to gel completely or to exhibit certain amounts of syneresis, whereas too much resin will result in a dry blend, i.e., a blend wherein not all of the resin is interacted with the gellant. In other words, the gellant will not completely wet the resin that is available. The final choice of gellant and resin will depend upon the properties desired, the fragrances used and the rate of release that is to be obtained.

While the rate of release of the reodorant from the compositions of this invention may be controlled by the optimization of ingredients contained therein, the rate may be further controlled by physical means. Since the gels function by the migration of the odor-releasing chemicals from within the matrix to the surface of the gel and thence into the surrounding atmosphere, it is obvious that by controlling the available surface area (e.g., through size or geometry) the rate of release of odorants into the atmosphere can be regulated. Therefore, gels having a single surface (such as when contained in a dish or a cup having sidewalls) will release their constituents at a slower rate and will be depleted less quickly than will gels having multiple surfaces (such as would be provided by a cube). Moreover, the gels can be wrapped or placed within a barrier such as an evelope made of a plastic such as polyethylene which serves to reduce the rate of diffusion of the volatile constituents into the surrounding atmosphere. An example of this would be to place the gel in a dish or cup and then cover the dish with a laminate seal which will inhibit diffusion until the seal is removed prior to use.

A very practical and preferred way of regulating the rate of release of odorant from the gel is by forming the gel in a dish thereby providing a single surface, and then placing the dish in a holder which is completely enclosed but which has vents or ventlike openings which can be placed in an open position or in a closed position or at any stage in between. When the gels are not in use, the holder can merely be turned to the "off" position until such time as further use is desired. When the gel is depleted, the dish can simply be removed from the holder and replaced with a similar dish containing fresh gel.

A further attractive feature of the present gels is that they shirnk at a predictable rate which is directly proportional to the loss of volatile constituents. This property can be utilized to give a visual indication of when the gel requires replacement. This can be accomplished by providing indicia on the bottom of the dish containing the gel (e.g., the word "replace") which can be viewed through a transparent opening in the holder. As the gel shrinks in thickness through loss of the volatile constituents, the indicia will become visible giving a visual signal of when the gel is exhausted and requires replacement.

Reodorant gels in accordance with the invention can be conveniently made by adding polyvinyl acetal resin in the form of a powder to the liquid gelling agent (plus diluent and fragrances if desired) with stirring to secure a homogeneous mixture which can be filled into suitable containers or into the holder itself. Upon setting the mixture will form into a firm, dry gel. If desired, the gellation state may be expedited by subjecting the mixture to an elevated temperature of about 50°C to 150°C before or after filling. The period of heating can vary from a few minutes to five hours or longer. After cooling to ambient temperature a firm, rubbery gel is formed which is dry to the touch. Alternatively, the gel mixture may be prepared directly in a mold or container or the holder in which it is to be used. The gels can further be formulated by casting, injection molding, extrusion of dry blends and other conventional means.

The gels can be formed in any desired shape such as sheets, rods, cubes, discs and strips, and can have one or more generating surfaces as previously discussed.

Upon storing, the shelf-life of these gels is satisfactory over an extended period of time with no evidence of odor shift or deterioration of fragrance. Preferably the gels are stored in an air-tight atmosphere, for example, encased in a laminated plastic film or in a metallic pouch, or in a plastic or metallic dish covered with a laminate seal.

If desired, small amounts of non-volatile plasticizers conventionally used for plasticization of thermoplastic resins can be added without adversely affecting the properties of the gels. Moreover these plasticizers also tend to increase the porosity of gel in the final stage which will permit the composition to be more completely depleted of the fragrance contained therein. Examples of such plasticizers are the lower alkyl esters of dibasic carboxylic acids such as dibutylphthalate, dioctylphthalate, di-2-ethylhexylphthalate, dioctyladipate, diisobutyladipate and the like.

Other conventional additives such as antioxidants, surfactants, dyes, deodorants, stabilizers, etc., can also be incorporated into the gels of the present invention.

The invention will now be further described by means of the following examples which are representative only, and should not be construed as limiting.

EXAMPLE I

Gels were made by combining a polyvinyl butyral polymer (PVB) having an average molecular weight of about 1.8 to 2.7 × $10^5$ and containing about 80% by weight of polyvinyl butyral units, 18–21% by weight of polyvinyl alcohol units and 0–2% by weight polyvinyl acetate units with the other ingredients in the amounts indicated below and mixing to form a homogeneous solution. The gels were cured at about 100°C for a period of about 2 to 4 hours. The cooled gels were firm, rubbery solids which were dry to the touch.

| Ingredients | % by Weight | | | | |
|---|---|---|---|---|---|
| | A | B | C | D | E |
| PVB | 20 | 20 | 21 | 21 | 20 |
| Menthone | 80 | 40 | | 42 | |
| Carvone | | | 42 | | 20 |
| Limonene | | 40 | 31 | 31 | 40 |
| Fragrance (Floral) | | | 6 | 6 | 20 |

The gels prepared above utilizing menthone (peppermint aroma) and carvone (spearmint aroma) as gelling agents were shown to be popular as bathroom air fresheners and provided an average vaporization rate of 10–15 mg/hr over a period of from 5 to 6 weeks. This compares to an efficacious period of only 12 to 15 days for a leading commercial aqueous-based reodorant gel, used under identical conditions of exposure.

EXAMPLE II

Gels were prepared by mixing the powdered PVB used in Example I with a gelling agent and optionally a diluent and a commercial fragrance in the proportions shown in the table below. After curing and weighing, the gels which generally had a cylindrical shape were placed into holders, some of which could be turned to an on or off position, and evaluated by a consumer test panel to determine their acceptability. At the end of their effective use life they were agin weighed and weight loss recorded and average vaporization rate (mg/hr) calculated. The formulations tested were as follows.

| Ingredients | % by Weight | | | | | | | | |
|---|---|---|---|---|---|---|---|---|---|
| | F | G | H | I | J | K | L | M | N |
| PVB | 20 | 20 | 20 | 20 | 20 | 20 | 21 | 20 | 23 |
| Menthone | 80 | 40 | | | 32 | 40 | | | |
| Carvone | | | 80 | 40 | 8 | | 42 | 40 | 44 |
| Limonene | | 40 | | 40 | 40 | 30 | 31 | 33 | 33 |
| Fragrance | | | | | | $10^a$ | $6^b$ | $7^c$ | |

$^a$Commercial Orange Fragrance
$^b$Commercial Floral Fragrance
$^c$Commercial Floral Fragrance The results of testing were as follows.

| Formulation | Initial Weight (g) | On-Off Holder Used | Use life* (Days) | Cumulative Wt. Loss (g) | Average Vapr. Rate (Mg/Hr) | Comments |
|---|---|---|---|---|---|---|
| F | 25 | No | 42 | 15 | 15 | $a$ |
| G | 25 | No | 59 | 10 | $7^d$ | $a$ |
| H | 25 | No | 56 | 9 | 7 | |
| I | 75 | Yes | 63 | 30 | 20 | $b$ |
| J | 50 | No | 40 | 25 | 9 | |
| K | 70 | Yes | 60 | 16 | 11 | $c$ |
| L | 48 | Yes | 41 | 21 | 20 | |
| M | 75 | Yes | 67 | 23 | 14 | |

| Formulation | Initial Weight (g) | On-Off Holder Used | Use life[e] (Days) | Cumulative Wt. Loss (g) | Average Vapr. Rate (Mg/Hr) | Comments |
|---|---|---|---|---|---|---|
| N | 45 | No | 91 | 21 | 9 | |

[a] Masked bathroom odor.
[b] Masked diaper odor in laundry room.
[c] Masked cooking odor.
[d] Single surface disc, i.e., gel contained in dish.
[e] Panel response varies due to olefactory sensitivity of individuals and concentration of fragrance in the available air space.

EXAMPLE III

The formulations indicated in the following table were prepared in 50 ml beakers by mixing PVB resin, as described in Example I, with various terpene aldehydes, ketones and alcohols shown in the table below. The weight ratio of PVB to liquid gellant was 1:4 except for Formulation R which contained just sufficient gellant to wet the PVB resin. Gellation was effected at ambient temperature; however, after gellation the gels were cured at 90°–100°C for 20 minutes to 1 hour. The gelling characteristics and the appearance of the gels after curing are recorded in the following table.

| Formulation | Gellant | Gelling Characteristics | Appearance After Curing |
|---|---|---|---|
| O | citronellal | relatively slow gellation (1–2 mins.) | dry, firm and rubbery, opaque |
| P | citral | average gellation (½–1 min.) | dry, firm and rubbery, clear |
| Q | menthone | relatively slow gellation (1–2 mins.) | dry, firm and rubbery, clear |
| R | l-carvone | rapid and obvious gellation | dry, firm and rubbery, some bubbles but otherwise clear |
| S | geraniol | rapid and obvious gellation | dry, but quite gummy and sticky, clear |

EXAMPLE IV

The following formulations were prepared by mixing the ingredients shown below at room temperature followed by curing at 95°C for about 1½ hours in foil covered beakers.

| Formulation T | | Formulation U | |
|---|---|---|---|
| PVB | 5 g | PVB | 5 g |
| Menthone | 10 g | Limonene | 16 g |
| Limonene | 10 g | | |

Formulation T containing limonene and menthone (an oxygenated terpene) formed a dry, rubbery gel, while Formulation T containing limonene alone did not form into a gel, but rather a solid plug (12 g) in admixture with liquid limonene.

EXAMPLE V

A series of gel formulations were prepared employing various resins both in accordance, and not in accordance, with the present invention. The formulations were prepared in 10 gram batches by mixing the ingredients of the formulations shown in the table below in 50 ml. beakers. The tops of the beakers were covered with aluminum foil, taped and allowed to stand at ambient temperature overnight. Thereafter the formulations were cured at 110°C in an electric air oven for 3 hours. The formulations comprised 20%w of the respective resins shown in the following table, 24%w of 1-carvone gellant, 32% of d-limonene and 24% of an oxygenated terpene-containing floral perfume.

| Formulation | Resin | Setting Characteristics | Appearance Before Curing | Appearance After Curing |
|---|---|---|---|---|
| AA | a | sets up rapidly | firm, dry and rubbery | firm, dry and rubbery |
| AB | b | sets up fairly quickly | quite sticky less rubbery than AA | slightly stickier and not as tough as AA |
| AC | c | sets up slowly | fairly tough gel, good matrix | not as tough as AA or AB |
| AD | d | some thickening no gellation | syrupy | syrupy |
| AE | e | sets up slowly | dry and rubbery, non-sticky | dry and rubbery, slightly softer than AA |
| AF | f | no gellation | no gellation | no gellation |
| AG | g | no gellation | no gellation | no gellation |
| AH | h | no gellation | no gellation | friable opaque gel, free liquid |
| AI | i | no gellation | no gellation | no gellation |
| AJ | j | slight thickening | no real gellation | brittle solid plug with free liquid | a - polyvinyl butyral described in Example I.
b - polyvinyl butyral having an average molecular weight (weight average) of 1.0 to 1.5 × 10⁵ and containing approximately 80% by weight of polyvinyl butyral units, 17.5-20% by weight of polyvinyl alcohol units and 0-2.5% by weight polyvinyl acetate units.
c - polyvinyl butyral having an average molecular weight of 0.5 to 0.8 × $10^5$ and containing approximately 80% by weight polyvinyl butyral units, 17.5-21.0% by weight polyvinyl alcohol units and 0-2.5% by weight of polyvinyl acetate units.
d - polyvinyl butyral having an average molecular weight of 0.34 to 0.38 × $10^5$ and containing approximately 88% polyvinyl butyral units, 9.0-13.0% by weight polyvinyl alcohol units and 0-2.5% by weight of polyvinyl acetate units.
e - polyvinyl butyral having an average molecular weight of 0.38 to 0.45 × $10^5$ and containing approximately 80% by weight polyvinyl butyral units, 18.0-20.0% by weight polyvinyl alcohol units and 0-1.0% by weight polyvinyl acetate units.
f - polyvinyl formal having an average molecular weight (weight average) of 0.24 to 0.4 × $10^5$ and containing approximately 82% by weight polyvinyl formal units, 5.0-6.0% by weight polyvinyl alcohol units and 9.5-13.0% by weight polyvinyl acetate units.
g - vinyl acetate-acrylic ester copolymer (Gelva V-7).
h - hydroxypropylcellulose having a molecular weight of about 900,000 (Klucel H).
i - carboxymethylcellulose (CMC 7H).
j - a synthetic hydrophilic gum (Carbopol 934).

The results presented in the foregoing table demonstrate the significance of the molecular weight, hydroxyl content and resin type in forming the gels of the present invention. Formulations AA, AB, AC and AE in accordance with the invention produced gels of generally satisfactory characteristics, while the remaining formulations prepared from resins not in accordance with the invention, or not having the requisite molecular weights or hydroxyl contents, produced inferior gels or no gels at all.

EXAMPLE VI

A series of gel formulations were prepared by mixing PVB polymer as described in Example I with an oxygenated terpene-containing floral perfume and various diluents in the proportions indicated in the following table. Curing was accomplished at 110°C for 1 hour. The characteristics of each of the gels after curing are shown below

| Formulation | Resin % by weight | Perfume-gellant % by weight | Diluent Type | % by weight | Gel Characteristics |
|---|---|---|---|---|---|
| AK | 20 | 48 | d-limonene | 32 | sets up well, firm, dry and rubbery |
| AL | 20 | 48 | amyl acetate | 32 | sets up well, slightly softer than AK |
| AM | 20 | 48 | phenethyl alcohol | 32 | sets up well, slightly softer than AL |
| AN | 20 | 48 | 2-octanone | 32 | sets up well, tougher than AL |
| AO | 20 | 48 | β-pinene | 32 | sets up well similar to AN |
| AP | 20 | 48 | octyl- aldehyde | 32 | sets up well, similar to AN |
| AQ | 20 | 48 | camphene | 32 | sets up well, even tougher gel than AN |

In addition to the foregoing gel formulations, a further formulation was prepared containing water with a suitable solubilizer in addition to an organic diluent. The composition of this gel was as follows:

| Formulation AR | % by Weight |
|---|---|
| Polyvinyl butyral (as described in Example I) | 20 |
| Oxygenated terpene-containing perfume | 44 |
| d-limonene | 26 |
| Water | 4 |
| Solubilizer (Triton X-100) | 6 |

What is claimed is:
1. A gelled slow-release air reodorant composition comprising (1) as a fragrance from about 5 to about 90% by weight of an acyclic or monocyclic terpene aldehyde, ketone, or alcohol in gelling interaction with (2) from about 10 to about 40% by weight of a polyvinyl acetal resin compatible with said terpene, said polyvinyl acetal resin having a molecular weight of from about 30,000 to about 1,000,000 and consisting essentially of repeating vinyl acetal, vinyl alcohol and vinyl acetate groups represented by the structure:

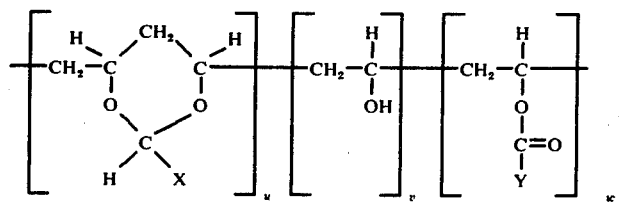

wherein X is H, alkyl of 1–8 carbon atoms, haloalkyl of 1–8 carbon atoms, hydroxyalkyl of 1–8 carbon atoms, alkenyl of 2–8 carbon atoms, halogen or hydroxyl; Y is alkyl of 1–9 carbon atoms; and $u$, $v$ and $w$ indicate the relative percent by weight of the respective vinyl acetal, vinyl alcohol, and vinyl ester groupings of the resin, and wherein $u$ is from about 30 to about 90, $v$ is from about 15 to about 25 and $w$ is from 0 to about 30, and the sum of $u + v + w$ equals 100.

2. The composition of claim 1 wherein X is $C_3H_7$ and Y is $CH_3$.

3. The composition of claim 2 wherein the reodorant gel additionally contains from 0 to about 90% by weight of perfume, from 0 to about 20% by weight water and from 0 to about 60% by weight organic diluent, said diluent being mutually compatible with said terpene gellant and said perfume.

4. The composition of claim 3 wherein the gellant is a terpene aldehyde or ketone having ten carbon atoms.

5. The composition of claim 4 wherein $u$ is from about 75 to about 85, $v$ is from about 17 to about 21, and $w$ is from 0 to about 5, and the average molecular weight of the polyvinyl acetal resin is from about 180,000 to about 300,000.

6. The composition of claim 5 wherein the amount of terpene gellant is from about 10 to about 30% by weight, the amount of the resin is from about 15 to about 30% by weight, the amount of organic diluent is from about 10 to about 50% by weight, the amount of perfume is from about 1 to about 60% by weight and the amount of water is from 0 to about 10% by weight.

7. The composition of claim 6 wherein the diluent is a menthadiene.

8. The composition of claim 7 wherein the terpene gellant is menthone or carvone.

9. The composition of claim 8 wherein the diluent is d- or l-limonene.

10. The composition of claim 9 wherein the terpene gellant is menthone.

11. The composition of claim 9 wherein the terpene gellant is carvone.

* * * * *